United States Patent [19]

Berndt

[11] Patent Number: 5,593,854

[45] Date of Patent: Jan. 14, 1997

[54] DATA ANALYSIS METHOD FOR USE WITH FLUORESCENT BACTERIAL SENSORS

[75] Inventor: Klaus W. Berndt, Stewartstown, Pa.

[73] Assignee: Becton Dickinson and Company, Franklin Lakes, N.J.

[21] Appl. No.: 197,033

[22] Filed: Feb. 16, 1994

[51] Int. Cl.$^6$ .............................. C12Q 1/22; C12Q 1/04; G01N 21/64

[52] U.S. Cl. .............................. 435/31; 435/34; 435/808; 422/82.07

[58] Field of Search .............................. 435/31, 34, 39, 435/808, 968; 356/39, 226, 307; 422/82.07, 82.09; 436/68, 167, 172

[56] References Cited

U.S. PATENT DOCUMENTS

| | | | |
|---|---|---|---|
| 4,945,060 | 7/1990 | Turner et al. | 435/291 |
| 5,030,420 | 7/1991 | Bacon et al. | 422/82.07 |
| 5,237,631 | 8/1993 | Gavish | 385/12 |
| 5,272,090 | 12/1993 | Gavish | 436/133 |
| 5,293,210 | 3/1994 | Berndt | 356/39 |

FOREIGN PATENT DOCUMENTS

| | | |
|---|---|---|
| 0448923 | 2/1991 | European Pat. Off. . |
| 0488923A1 | 10/1991 | European Pat. Off. . |
| 4213235 | 10/1993 | Germany . |
| 2132348 | 7/1984 | United Kingdom . |

OTHER PUBLICATIONS

Berndt K., Electroluminescent Lamp Based Phase . . . Anal Biochem 201 pp. 319–325 1992.
Nolte F., Multicenter Clinical Evaluation of a . . . J of Clinical Micro 31(3) Mar. 1993 pp. 552–557.

Primary Examiner—Ralph Gitomer
Attorney, Agent, or Firm—A. W. Fiedler

[57] ABSTRACT

A method of analyzing the data provided by a fluorescent chemical sensor calculates a ratio based on the AC and DC components of the emission from the chemical sensor. This ratio, or the emission modulation, will change should bacterial growth be ongoing in the vial. The calculated ratio is compared to a desired value. The desired value is selected to focus the operation of the system into a high resolution area for the sensor. If the calculated and desired ratios differ, then the frequency of the excitation radiation is changed until the calculated and desired ratios are effectively equal. At that time the adjusted frequency is measured. By focusing the desired ratio into a high resolution area, and adjusting the frequency until the system reaches that ratio one ensures that all readings are performed at a high resolution area of the sensor. The adjusted frequency is utilized to provide an indication of whether the particular vial is experiencing bacterial growth. This adjusted frequency is a linear function of changing conditions within the vial. Several methods of achieving the above features of this invention are disclosed. By utilizing this method, one provides an easily interpreted indication of whether a particular fluorescent chemical sensor is in a vial which is experiencing bacterial growth.

11 Claims, 8 Drawing Sheets

5,593,854

DATA ANALYSIS METHOD FOR USE WITH FLUORESCENT BACTERIAL SENSORS

This application relates to an improved method for interpreting data from fluorescent chemical sensors used to detect bacteria in body fluid samples. The present inventive method provides a linear output that is more accurate and more readily utilizable than prior art methods.

In the prior art, a wide variety of so-called non-invasive chemical sensors are utilized with body fluid samples to provide an indication of whether bacterial activity is ongoing in the sample. As is known, a body fluid sample, such as blood, is injected into a vial containing a culture medium. A chemical sensor has been previously placed within the vial. The vial is then incubated and monitored for bacterial growth. Several known types of instruments are utilized to monitor the bacterial growth by detecting the changes in the chemical sensors.

A first known type of chemical sensor responds to changes in conditions within the vial, such as a change in oxygen concentration, by changing the intensity of radiation directed into the sensor. Thus, by monitoring the radiation intensity emerging from the sensor, one can predict whether bacterial activity is ongoing in the vial. These types of sensors have enjoyed some success, but there are some deficiencies with their use.

One practical deficiency occurs since an actual apparatus typically tests hundreds of vials at one time. Each of the vials is equipped with its own light source and photodetector. Station-to-station variations between each of the hundreds of light sources and detectors may result in some variations in the readings. For this and other reasons, intensity based detection systems have not always proven fully satisfactory.

A second type of chemical sensor is a so-called fluorescent sensor that changes its fluorescent lifetime in response to changes in conditions within the vial. Such fluorescent sensors are not as sensitive to station-to-station variations and, thus, address the above-discussed problem. Many fluorescent sensors are known which change their fluorescent lifetimes with changing carbon dioxide concentration, oxygen concentration, or other chemical parameters. The present invention does not relate to a change in any chemical sensors, but rather to a change in the way that the fluorescent emissions from such chemical sensors are analyzed.

Typically, a change in the sensor fluorescent lifetime has been monitored by applying the phase shift method. Basically, an intensity-modulated excitation radiation source is directed into the chemical sensor. An intensity-modulated fluorescent emission results that is phase shifted related to the excitation radiation. Instruments read the phase shift angle from the emission radiation. The phase shift angle changes with changing conditions within a vial, and by monitoring the phase shift angle over time a prediction can be made as to whether a particular vial is experiencing bacterial growth.

Problems exist with the phase shift method, as will be explained by the following mathematical analysis. A phase shift angle $\Theta$ is dependent on the fluorescent lifetime $\tau$ according to the equation:

$$\tan \Theta = \omega \tau \quad (1)$$

In equation 1, $\omega$ is equal to $2\pi f$, and is known as the circular light modulation frequency. The f quantity is the frequency of the excitation light directed into the chemical sensor. The $\tau$ function changes, and is the component which is indicative of whether the specimen is experiencing bacterial growth. Typically, in the prior art, the $\omega$ component remains constant.

In equation 1, a main disadvantage of the phase shift method of monitoring the emissions of fluorescent sensors can be explained. If $\omega$ is small, then the phase shift angle would also be small. Thus, the resolution of the chemical sensor arrangement with regard to the changing chemical state that is being sensed is limited. That is, if the $\omega\tau$ quantity is small, the resolution with regard to change in, as an example, oxygen concentration, is also limited. A change in the measured phase shift angle $\Theta$ for a given change in $\tau$ (which may be dependent on oxygen concentration, as an example) would be relatively small and difficult to distinguish.

To overcome this resolution problem, the modulation frequency, f could be increased. However, the resulting phase shift angles would be compressed as they approach the range of 70–°90°. The maximum possible phase shift angle is 90°. Since tan $\Theta$ would be equal to infinity at 90°, the phase shift angle cannot actually ever reach 90°. Further, as the $\Theta$ angle approaches 90° the result of the test would become of little value.

Due to these limitations, the practical range of analyzing chemical sensor emissions based on the phase shift method is limited. Other limitations of the phase shift method can be seen by reviewing prior art FIGS. 1 and 2.

In FIG. 1, the solid curve shows phase shift angle $\Theta$ plotted as a function of the frequency lifetime product $\omega\tau$. The derivative of $\Theta$ due to $\tau$ is plotted by the dashed line. In this graph, $\omega$ is kept constant, and $\tau$ changes. As can be seen, the maximum changes occur under the condition $\omega\tau=1$. This condition would be achieved with a phase shift angle of 45°, point B in FIG. 1. As is also shown by the dashed derivative line curve, high sensor resolutions are obtainable over a very limited frequency lifetime range. The resolution is tied to the changes in $\Theta$, with a corresponding change in $\tau$. As can be seen, the change in $\Theta$ with change in $\tau$ soon moves to very small amounts. With the phase shift method, it would be desirable to have larger changes in $\Theta$, because it is these changes that are to be monitored to determine the conditions in the vial. Thus, if the $\omega$ quantity is kept constant, only a very limited range $\tau$ would result in a high sensor resolution. This limited range is a serious disadvantage for analyzing data from fluorescent sensors using the phase shift method.

Another problem with the phase shift method of analyzing the fluorescent emissions is illustrated in FIG. 2. FIG. 2 plots the phase shift angle $\Theta$ as a function of oxygen concentration c for a chemical sensor having a change in fluorescent lifetime based on oxygen concentration. The $\omega$ value is kept constant.

By the Stern-Volmer equation $\tau$ can be calculated as follows:

$$\tau = \frac{\tau_0}{1 + kc} \quad (2A)$$

Taking equation 1 and 2A together, it can be shown that the phase shift angle $\Theta$ is given by the equation:

$$\Theta = \arctan \frac{\omega \tau_0}{1 + kc} \quad (2B)$$

In equation 2B, k is a constant. The $\tau_0$ quantity is based upon $\tau$ in the absence of oxygen. In FIG. 2, $\omega\tau=\sqrt{2}$. During operation of the sensor, the product $\omega\tau$ runs between maximum value $\omega\tau_0$, when no oxygen is present, to a very low value for high oxygen concentrations. The resolution of the sensor varies over this range, as is shown above.

As shown in FIG. 2, the $\Theta$ readings are highly non-linear. In order to utilize these $\Theta$ readings to make a determination of whether a particular sample vial is experiencing bacterial growth, one must make readings over time. As is shown in FIG. 2, the phase shift angle decreases with increasing oxygen concentration. In an oxygen-based chemical sensor, the presence of bacteria will result in a decrease in oxygen concentration. In the illustrated sensor, by studying changes in the phase shift angle $\Theta$ over time, and by looking for an increase in phase shift angles, one can determine whether bacterial growth is ongoing in a particular sample vial.

Thus, two deficiencies with the phase shift method can be summarized as follows. First, high resolutions of the sensors are limited to a very small operational range. The $\omega$ value is typically constant. This results in the quantity $\tau$ being limited to a very narrow band for high sensor resolution. That is, only a very limited band of, for instance, oxygen concentration changes would come within a high sensor resolution area for the particular chemical sensor. If the sample vial is outside of that range, only low sensor resolution will be provided, and the resulting readings may be difficult to analyze.

Further, as explained above, one must read the phase shift angles and look for changes over time. Due to the non-linear nature of the phase shift change with the changing oxygen concentration, these changes are difficult to read over time. As an example, during the relatively small change area between 20 percent to 50 percent concentration shown at FIG. 2, only small changes in $\Theta$ would be expected. During the very rapid changes between 0 percent and 10 percent, a small change may appear on a reading as being a very large change in oxygen concentration. The prior art has attempted to overcome this problem, but the non-linear changing values still present difficulties.

For the foregoing reasons, the phase shift method has not proven fully satisfactory as a method of analyzing fluorescent emissions from chemical sensors based on changing fluorescent lifetimes.

SUMMARY OF THE INVENTION

The present invention provides a method of evaluating fluorescent emissions from a chemical sensor. In the inventive method, a ratio based on the emission is compared to a desired ratio. The frequency of the excitation input is changed if the measured ratio differs from the desired ratio. The input frequency continues to be adjusted until the measured and desired ratios are effectively equal. In this way, the $\omega$ quantity is changed, as the $\tau$ quantity changes. The desired ratio is selected to focus the $\tau$ quantity in a high resolution area. The $\tau$ quantity is changing with changing conditions in the sample vial. The changing $\omega$ quantity is thus indicative of a change in the $\tau$ quantity, which is, in turn, indicative of a change of the parameter being measured, such as oxygen concentration. In the invention this adjusted $\omega$ quantity is used to determine whether a particular sample vial is evidencing a bacterial growth. In fact, it is the f component of $\omega$ which is used, but the two values are proportional.

As will be shown below, when evaluated using this method, the f quantity will change linearly with the changing oxygen concentration. Thus, not only can the inventive method be used to focus the $\omega\tau$ quantity into the narrow high resolution sensor band, but further, the resulting $\omega$ quantity is a linear function of changes in oxygen. Thus, the inventive results are easy to interpret and utilize.

In one inventive method of evaluating fluorescent emissions, the ratio is based on the AC and DC components of the emission. This ratio is also known as the emission modulation. A ratio is taken of the AC and DC components and compared to a desired ratio. The desired ratio is preferably calculated to be the ratio that would be expected at a high resolution area for the particular sensor. If the measured and desired ratios differ, then the excitation frequency is changed, and the readings are again taken. These steps continue until the measured ratio is effectively equal to the desired ratio. The adjusted frequency is then measured and plotted on a graph. By comparing the changes in this adjusted frequency over time, one can make a determination of whether a particular sample vial is experiencing bacterial growth.

In an alternative method of evaluating the fluorescent emissions, the ratio may be based on the relative modulation, which compares the emission modulation to the modulation degree of the excitation light. In this second method, the ratio of the emission modulation and excitation modulation are compared to a desired ratio. As with the first method, the frequency of the excitation radiation is adjusted until the measured and desired ratios are equal. At that time, the excitation frequency is measured and plotted.

In a preferred embodiment of this invention, the input or excitation radiation is periodically turned off, and DC measurements are made. In this way, so-called dark signal readings can be canceled out from the measured DC quantities. This results in an even more accurate reading from the system.

Several embodiments of systems capable of performing the method of this invention are disclosed. It should be understood, however, that the main features of this invention relate to its inventive realization that by adjusting the excitation frequency to result in a measured ratio which is equal to a desired ratio, one may ensure that all readings are performed in the high resolution band for the sensor and, further, that the measured values are a linear function of changes in the chemical parameter to be measured.

These and other features of the present invention can be best understood from the following specification and drawings, of which the following is a brief description.

DETAILED DESCRIPTION OF THE PREFERRED EMBODIMENTS

As explained above, the present invention provides a fluorescent lifetime chemical sensor which ensures that readings are taken in a high resolution area of the sensor, and further results in a linear output function for the changing chemical parameter. These features will be explained mathematically and shown to be true experimentally below. Applicant will then disclose several systems for achieving the inventive method.

When a radiation source illuminates a chemical sensor material with an intensity-modulated excitation light, the fluorescent light emission shows a modulation degree $m_F$ given by the known equation:

$$m_F = \frac{m_E}{[1+(\omega\tau)^2]^{1/2}} \quad (3)$$

As stated above, the emission modulation $m_F$ is equal to the ratio of the AC and DC components of the emission radiation. The excitation modulation $m_E$ is equal to a ratio of the AC and DC components of the excitation radiation.

A relative modulation m for the fluorescent signal, can be defined as:

$$m = \frac{m_F}{m_E} \quad (4)$$

It is relatively safe to assume that the $m_E$ component is effectively 100%. Thus, in a broad method we make the assumption that we need to calculate only the emission modulation $m_F$, to arrive at accurate results. A final embodiment calculates both emission and excitation modulation and thus measures the actual relative modulation.

Figure 1:
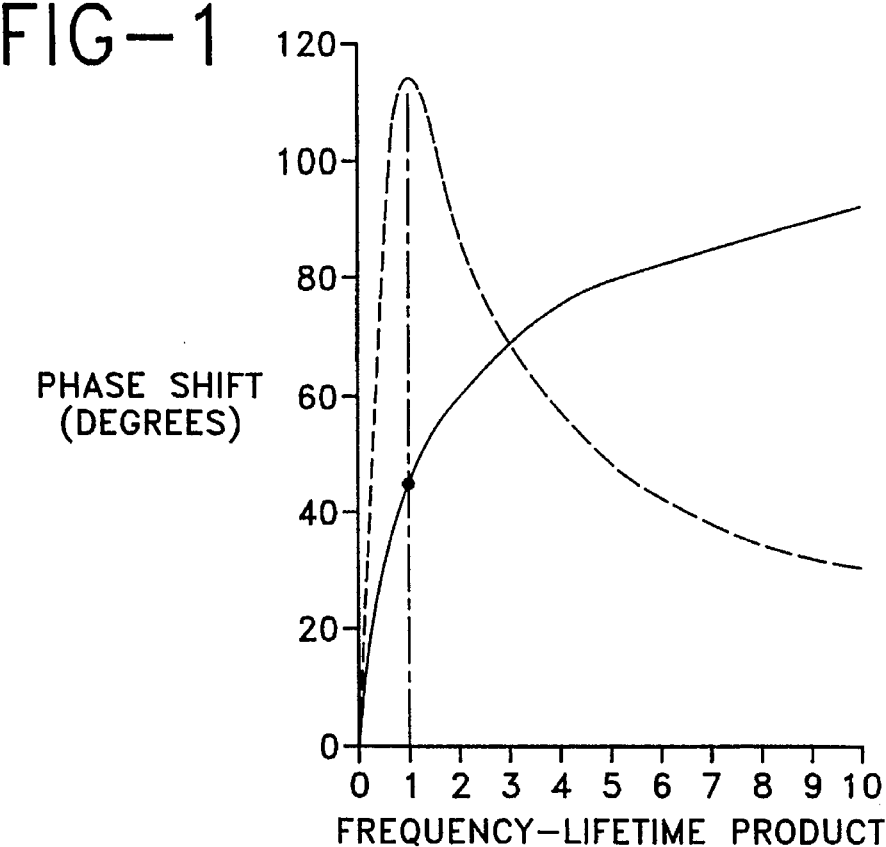
FIG. 1 is a graph showing feature of prior art methods.
Figure 2:
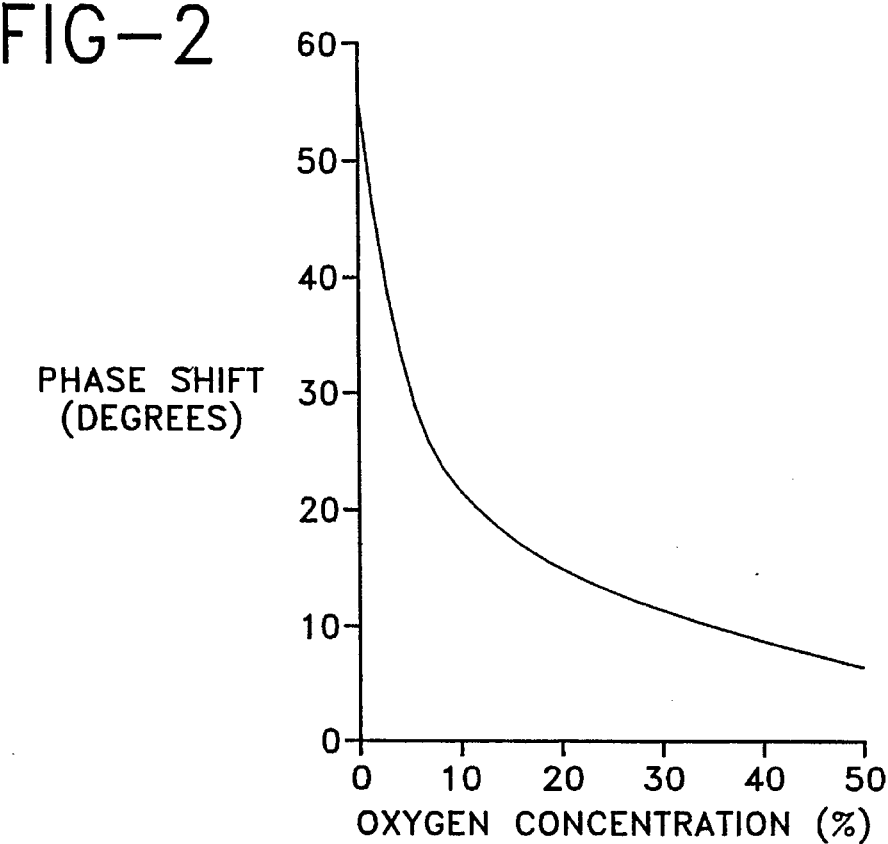
FIG. 2 is a second graph showing other features of prior art methods.
Figure 3:
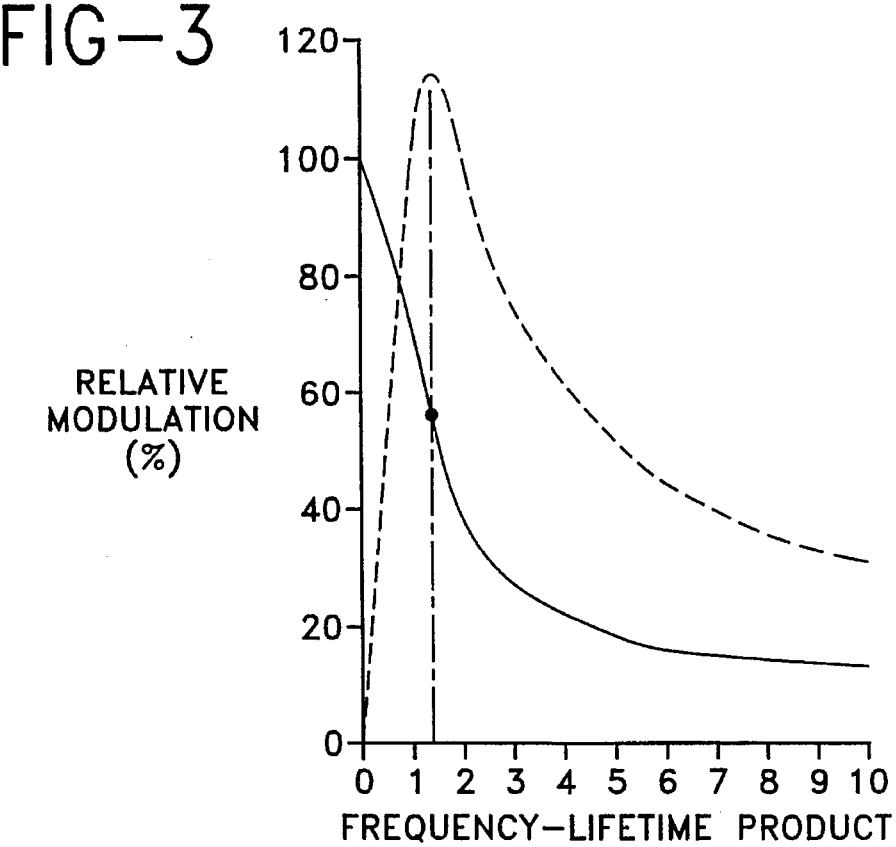
FIG. 3 is a graph explaining features of the inventive method.

FIG. 3 shows relative modulation m versus the $\omega\tau$ frequency-lifetime product. The value of m varies as shown by the solid curve in FIG. 3. The change in modulation m per relative change in the fluorescent lifetime is of interest. The higher value of the change in modulation, or the derivative of m per change in $\tau$, the better the sensor resolution. The quantity $dm/(d\tau/\tau)$ can be derived from equations 3 and 4, and is shown as the dashed curve in FIG. 2. As is shown in FIG. 3, the highest sensor resolution is achieved at the condition A where $\omega\tau$ equals the $\sqrt{2}$.

In the present invention, the ratio of the AC and DC components is directed to a comparator unit which compares the measured ratio to the desired ratio. The input frequency is adjusted if appropriate. The comparator unit is set such that it will have a voltage of zero when the two ratios are equal. The desired ratio is set to the situation in FIG. 3 when $\omega\tau$ is equal to the $\sqrt{2}$; that is, when m equals $1/\sqrt{3}$ (about 58%). Again, since we are assuming $m_E$ equals 100 percent, we need only measure the $m_F$ quantity.

As the quantity $\tau$ changes, differences between the measured and desired ratios will occur. This, in turn, will result in a control signal to the input for the excitation radiation directed into the chemical sensor, which will change its frequency. These changes in frequency will eventually result in the desired and measured ratios being equal. At that time, the adjusted frequency will be measured.

In a sense, the optical sensor arrangement according to this present invention is "locked into" the optimum operating condition for the particular sensor. In the illustrated example it is locked into the situation where $m=1/\sqrt{3}$.

We will now show that the adjusted frequency will be a linear function of the oxygen concentration. If we fix m at $1/\sqrt{3}$ then, from equations 3 and 4 it can be shown that:

$$f = \frac{1}{\pi\sqrt{2}\,\tau} \quad (5)$$

This shows that the modulation frequency f is inversely proportional to the fluorescent lifetime $\tau$.

As noted above, the lifetime $\tau$ is described (by the Stern-Volmer equation) as follows:

$$\tau = \frac{\tau_0}{1+kc} \quad (2A)$$

$\tau_0$ is the fluorescent lifetime in the absence of any of the quencher (oxygen, etc.). c is the quencher or analyte concentration, or quantity to be measured. As an example, c may be the oxygen concentration, and k is a quenching constant. By combining equations 5 and 2A, the resulting sensor modulation frequency f is shown to be:

$$f = \frac{1}{\pi\tau_0\sqrt{2}}(1+kc). \quad (8)$$

Equation 8 indicates that f is a linear function of the concentration of the quantity to be measured, c.

Figure 4:
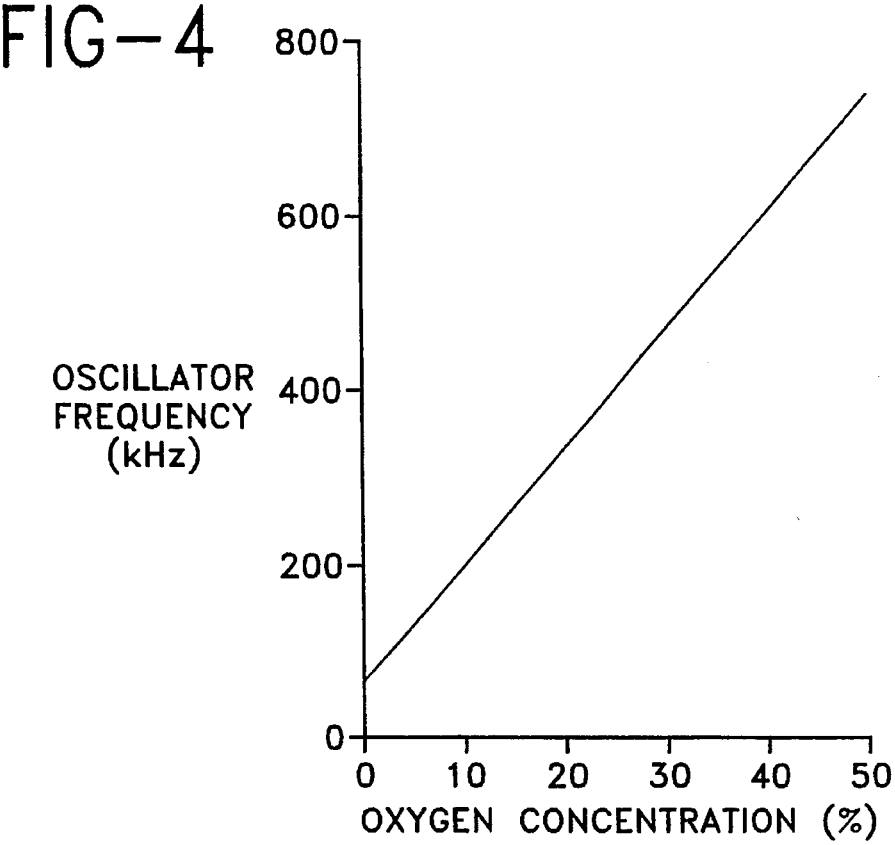
FIG. 4 is a graph showing features of the present invention.

FIG. 4 illustrates f for a chemical sensor based upon oxygen concentration. As shown, the frequency f would be a linear function of this oxygen concentration.

Figure 5:
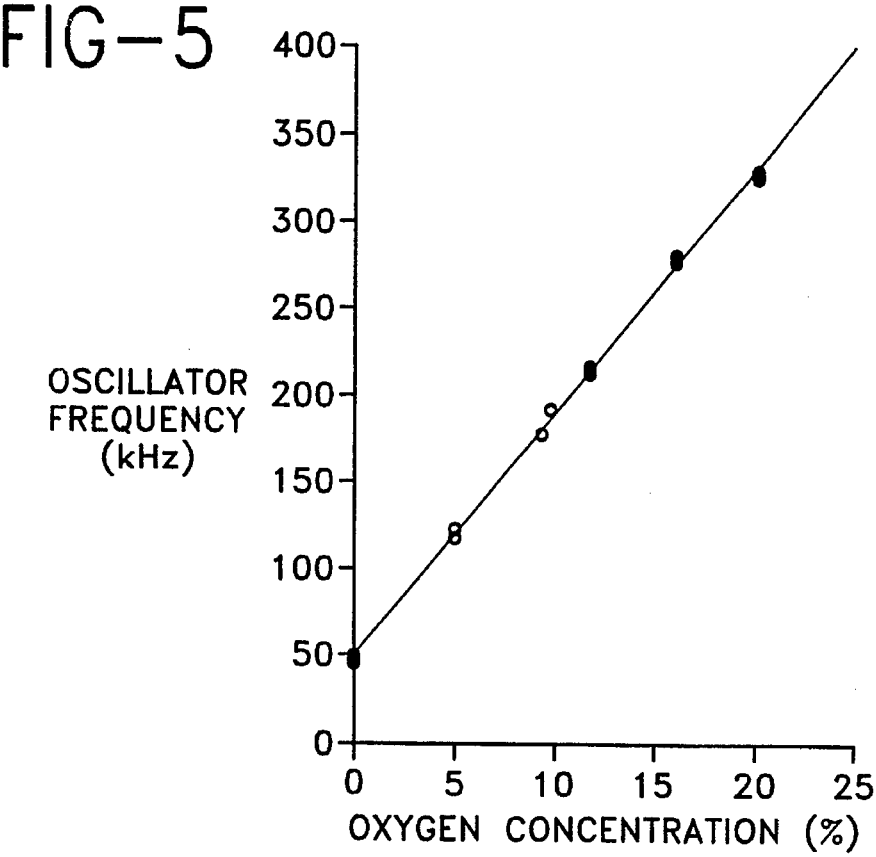
FIG. 5 shows experimental results based on the present invention.

FIG. 5 illustrates experimental results of a series of sample vials having oxygen concentrations of 0 to 21 percent, which were evaluated utilizing the inventive method. As shown, the resulting oscillator frequency is experimentally proven to be a linear function of the oxygen concentration.

Figure 6:
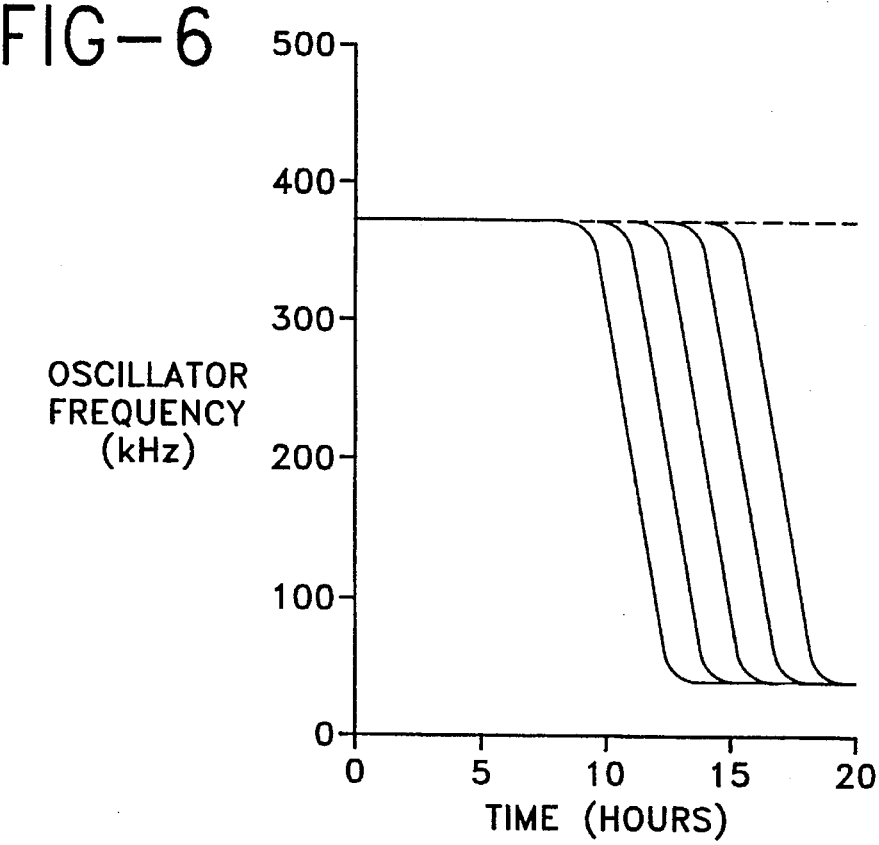
FIG. 6 shows calculated results based on the present invention.

FIG. 6 illustrates predicted results with the use of the present inventive method. As shown, at the beginning of time monitored, oxygen is present. The fluorescent decay time is thus short, resulting in a high oscillator frequency. After some time (which would depend on the particular micro-organism or bacteria species), oxygen is consumed which results in a longer fluorescence decay time, and consequently lower oscillator frequencies. Once most of the oxygen is consumed, the bacterial growth process comes to an end, and the oscillator frequency will reach a final value. As shown, by monitoring the oscillator frequency over time, one can make a determination of whether a particular sample vial is a positive. The positives are shown moving from the higher value oscillator frequency to the lower value. The five positive sample vials shown change within a relatively short span of time, and with relatively constant slopes of change lines. As further shown, a negative vial would have no change in oscillator frequency. Experimental results are shown to follow the results illustrated in this figure.

Figure 7:
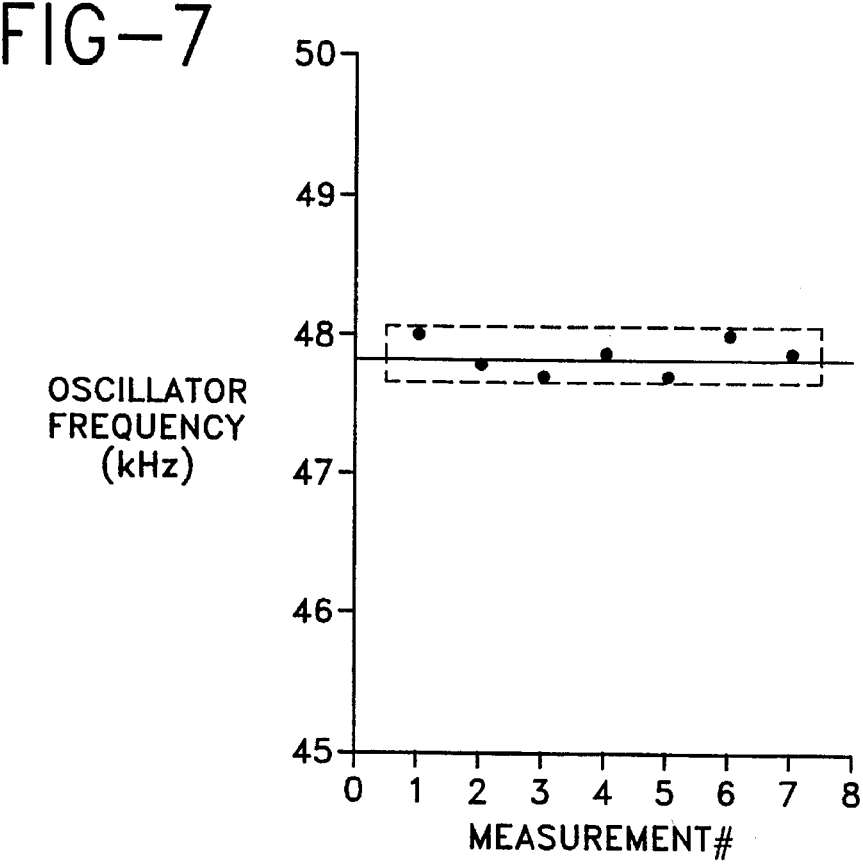
FIG. 7 shows further experimental results based on the present invention.

FIG. 7 illustrates experimental results of adjusted sensor frequency for a vial which has been repeatedly removed and then reloaded. The resulting frequency variation is shown to be only plus or minus 0.2 kH$_z$, corresponding to a variation in measured oxygen concentration of only plus or minus 0.015%. In intensity based systems, the positioning of the vial could result in some variations in the measured readings. Technicians periodically remove the vials and perform a visual check for bacterial growth. Thus, it is important that a method for analyzing the data be insensitive to repositioning. Decay time-based fluorescent sensor methods, such as the phase shift method, are relatively insensitive to repositioning. Thus, it is helpful to know that this inventive method is also insensitive to repositioning. This is borne out by the experimental results shown in FIG. 7, wherein the removal of the vial does not result in any significant changes in the frequency.

Figure 8:
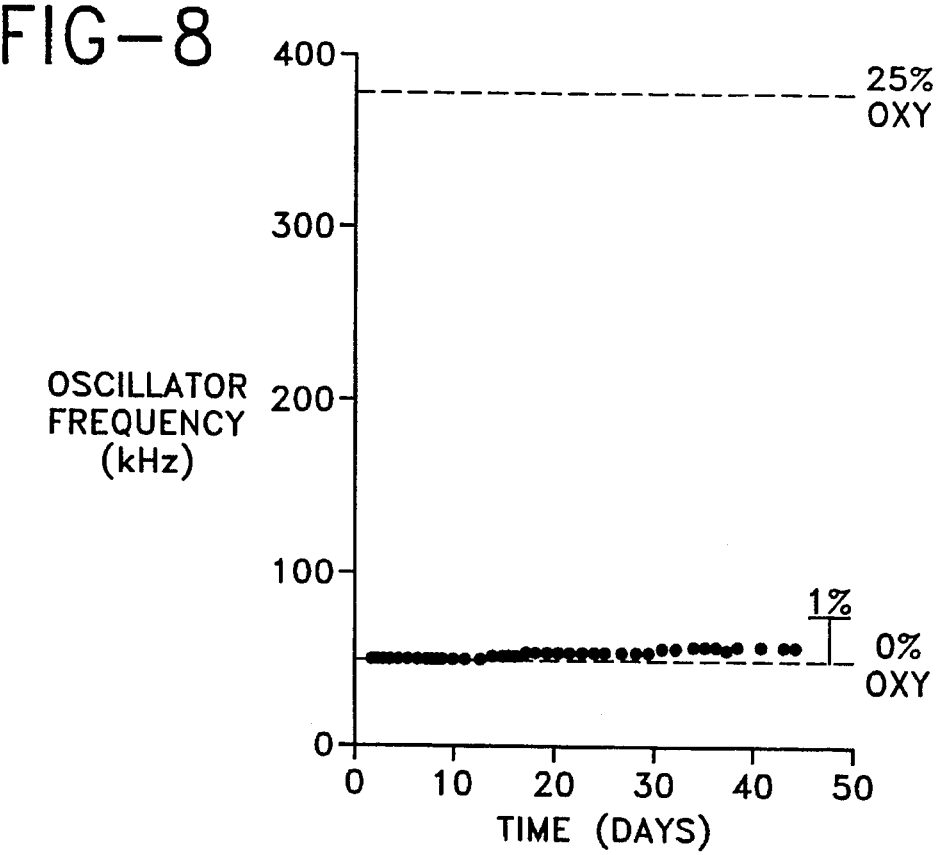
FIG. 8 shows further experimental results based on the present invention.

FIG. 8 illustrates experimental results of a long-term stability test for a vial having no oxygen. The sensor drift is shown over a period of 42 days as being only 0.5 percent of oxygen concentration. Due to the lack of oxygen in the vial, this small amount of oxygen could actually be the result of seepage, rather than some problem with the data analysis methods of this invention. Again, it is important to learn that the inventive method would not have any such sensor drift.

Figure 9:
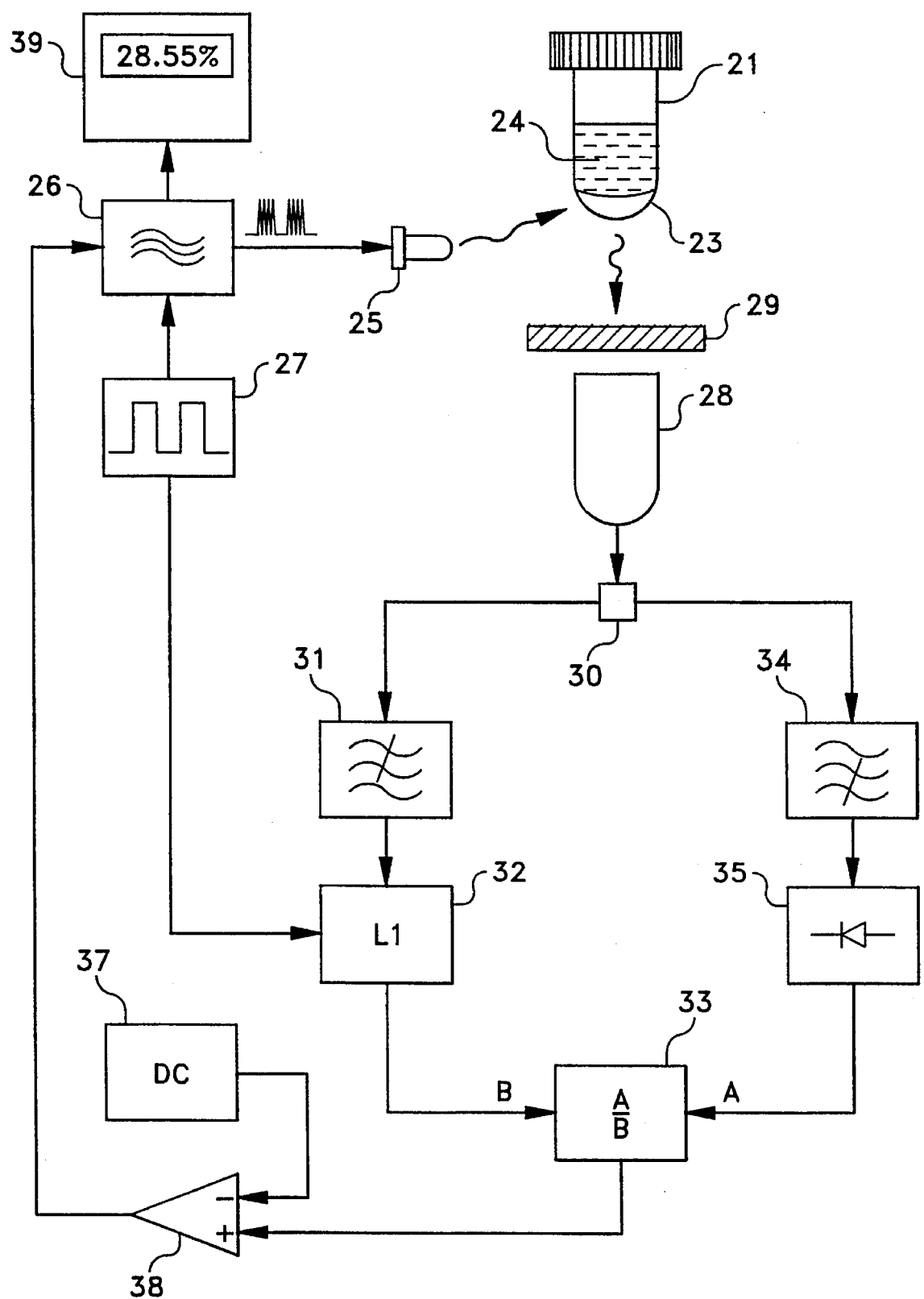
FIG. 9 shows a first system for accomplishing the method of the present invention.

FIG. 9 shows a first system for achieving the inventive method. As shown in FIG. 9, a vial 21 receives a culture medium 24. A chemical sensor 23 is placed on a bottom surface of vial 21. An excitation radiation source 25, which is preferably a blue or green LED, directs excitation radiation into the sensor 23. Radiation source 25 is connected to an electronic signal source 26 which provides a DC bias and a high-frequency modulation voltage. Signal source 26 receives a first and second control input. The first control input allows the source to be turned on and off. This control input is connected to the output of the low-frequency square-wave generator 27. The on/off feature is utilized to periodically take "dark" readings for the DC current. This will allow the elimination of background light from the calculation as will be described below. The second control signal provides for frequency control, as will be described below. Fluorescent light emerging from sensor material 23 due to the excitation radiation from source 25 is detected by a photodetector 28. An emission filter 29 may be disposed between sensor material 23 and photodetector 28 to reject back-scattered excitation light. The output of photodetector 28 is fed to power splitter 30, which splits the emission radiation. One output of power splitter 30 is connected to the input of a low pass filter 31, the output of which is fed to the signal input of a lock-in amplifier 32. The output of the lock-in amplifier 32 is connected as the B-input of an A/B ratio unit 33. This is indicative of the DC component from the emission radiation. Also, lock-in amplifier 32 is connected with the low-frequency square wave generator 27.

Power splitter 30 has its second output fed to the input of a high-pass filter 34. Filter 34 is connected via high-frequency volt meter 35 to the A input of the A/B ratio unit 33. This is indicative of a rectified AC component of the emission radiation.

The output of ratio unit 33 and a DC power supply 37 are connected to the two inputs of an integrating comparator 38. Comparator 38 is connected with the second control input for the frequency of electronic signal source 26. Electronic signal source 26 has an output which is connected to an electronic frequency counter 39.

As should be understood from the above description, radiation source 25 directs radiation into sensor 23. Sensor 23 emits radiation which is indicative of the conditions within vial 24. That emission radiation is detected by photodetector 28. A ratio of the AC and DC components of that emission radiation is provided to comparator 38. Comparator 38 compares that ratio to a desired ratio. If the ratios are different, a voltage signal is developed. This voltage signal is received by electronic signal source 26 to control the frequency of the radiation directed from radiation source 25 into sensor 23. This process is ongoing until the ratios of the measured radiation and the desired ratio are found to be effectively equal by comparator 38. Of course, some error margin can be developed such that the inventive method need not achieve absolute accuracy between the measured and desired ratios.

Figure 10:
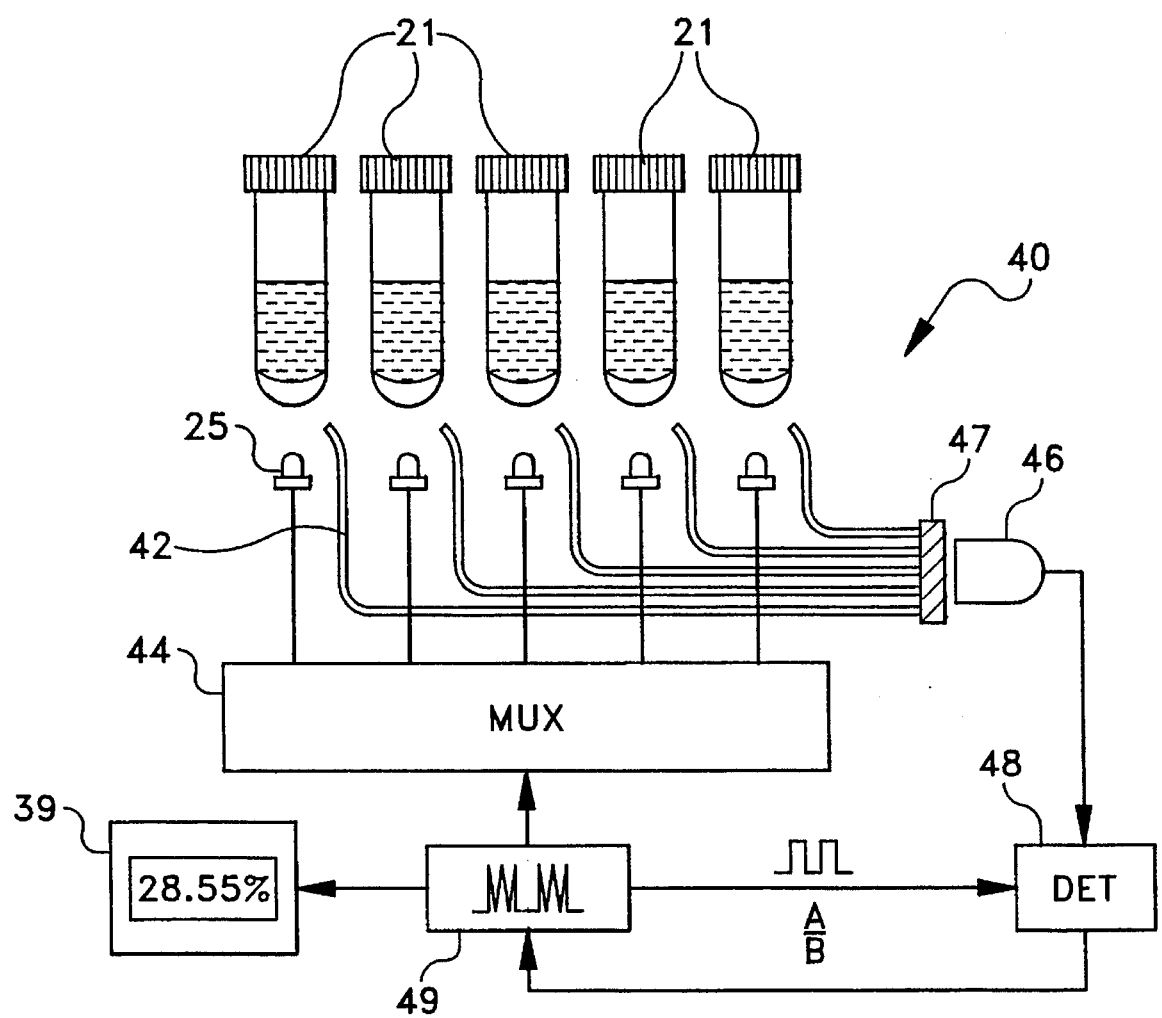
FIG. 10 shows a second system for accomplishing the method of the present invention.

A modification of the system shown in FIG. 9 for a plurality of vials 21 is illustrated in FIG. 10. Adjacent to each vial 21, an LED 25 is disposed, as is the input of a fiber 42. All of the LED's 25 are connected to a multiplexer 44, inputs of which are fed to the output of an electronic signal source 26. The output of all fibers 42 are bundled together and arranged at the optical output to a photodetector 46. An emission filter 47 is mounted between the fiber bundles and photodetector 28, again to remove back-scattered light. The remaining controls are generally similar to that illustrated in FIG. 9, and are shown by black box representations.

Figure 11:
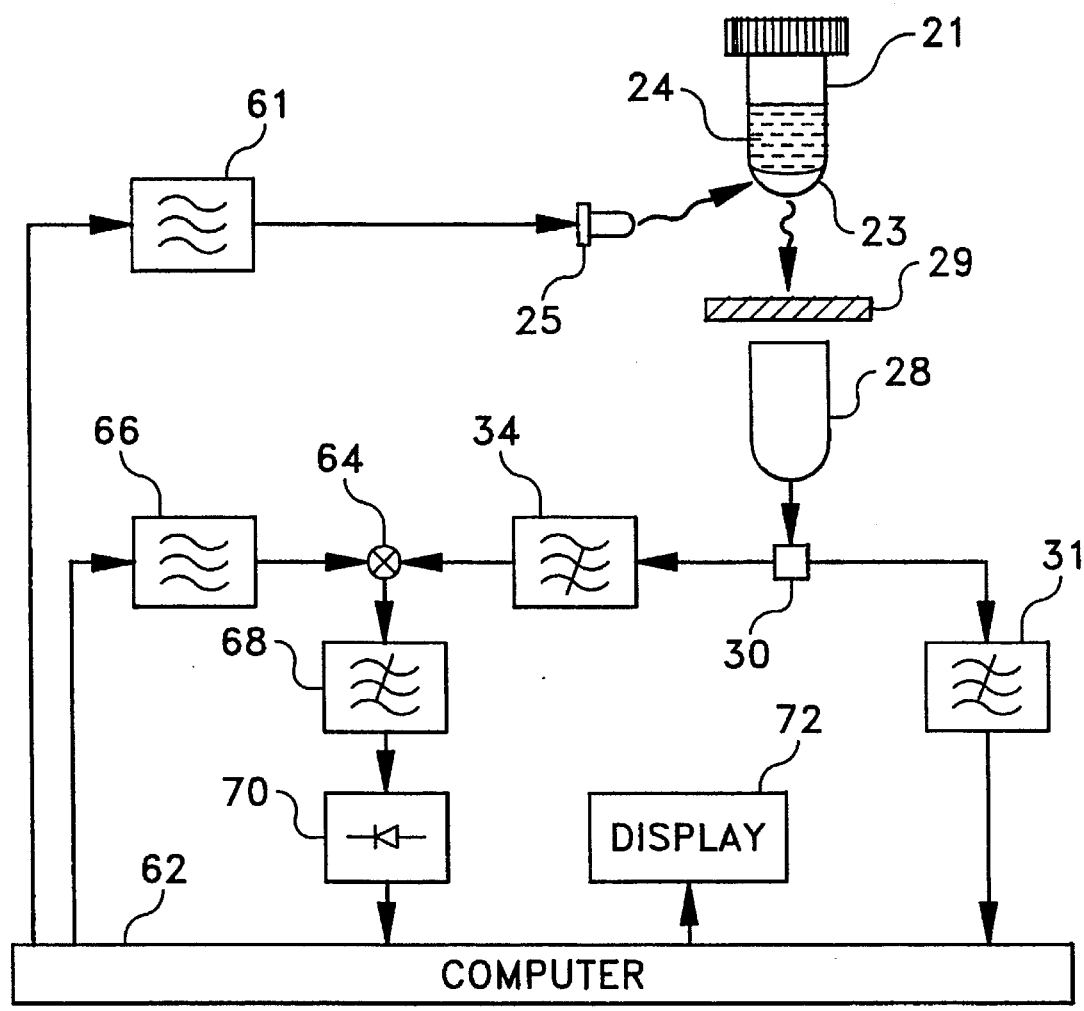
FIG. 11 shows a third system for accomplishing the method of the present invention.

FIG. 11 shows a third embodiment system according to the present invention. Vial 21 receives the chemical sensor 23. An excitation radiation source 25 is positioned adjacent to vial 21. The source 25 is connected to a first electronic signal source 61 which provides a DC bias and a high frequency modulation voltage at frequency f1. Signal source 61 is equipped with a frequency control input connected to a computer 62. Emission from the sensor material 23 are detected by photodetector 28. Photodetector 28 is connected to splitter 30. One output of the splitter 30 is connected to the input of a low-pass filter 31, the output of which is fed to the computer 62 as the DC component. Computer 62 comprises standard analog-to-digital convertors, and measures the DC component which passes through the filter at 31. The other output of the power splitter 30 is fed via a high-pass filter 34 to the RF input of an electronic broad band mixer 64. This embodiment also comprises a second electronic signal source 66 which is equipped with a frequency control input connected to computer 62. The output of the second signal source 66 is fed at a frequency f2 to the LO input of mixer 64. The IF output of mixer 64 is connected via a second low-pass filter 68 to the input of an AC volt meter 70. The output of volt meter 70 is fed to the computer 62 as the AC component. Computer 62 is equipped with a standard optical data display such as is shown schematically at 72.

The comparison of measured and desired ratios and the adjustment of the frequencies with this embodiment is similar to that disclosed above. In this modification, however, the frequency f2 is maintained at a small difference from frequency f1. The signal leaving the second electronic signal source 66 has a constant magnitude at the frequency f2. When the frequency at first electronic signal source 61 is changed during the measurement of the emissions from sensor 23, the frequency t2 is also changed to maintain the set difference. The signal seen by filter 68 is a low frequency signal, and the low-pass filter 68 can be utilized. The high frequency AC component is thus transferred into a low-frequency signal. By selecting a small frequency difference for f1 and f2, the detection band-width can be made extremely narrow, resulting in an increased signal-to-noise ratio for the AC component. The use of mixer 64 also provides the advantage of a conversion gain for the RF signal.

Figure 12:
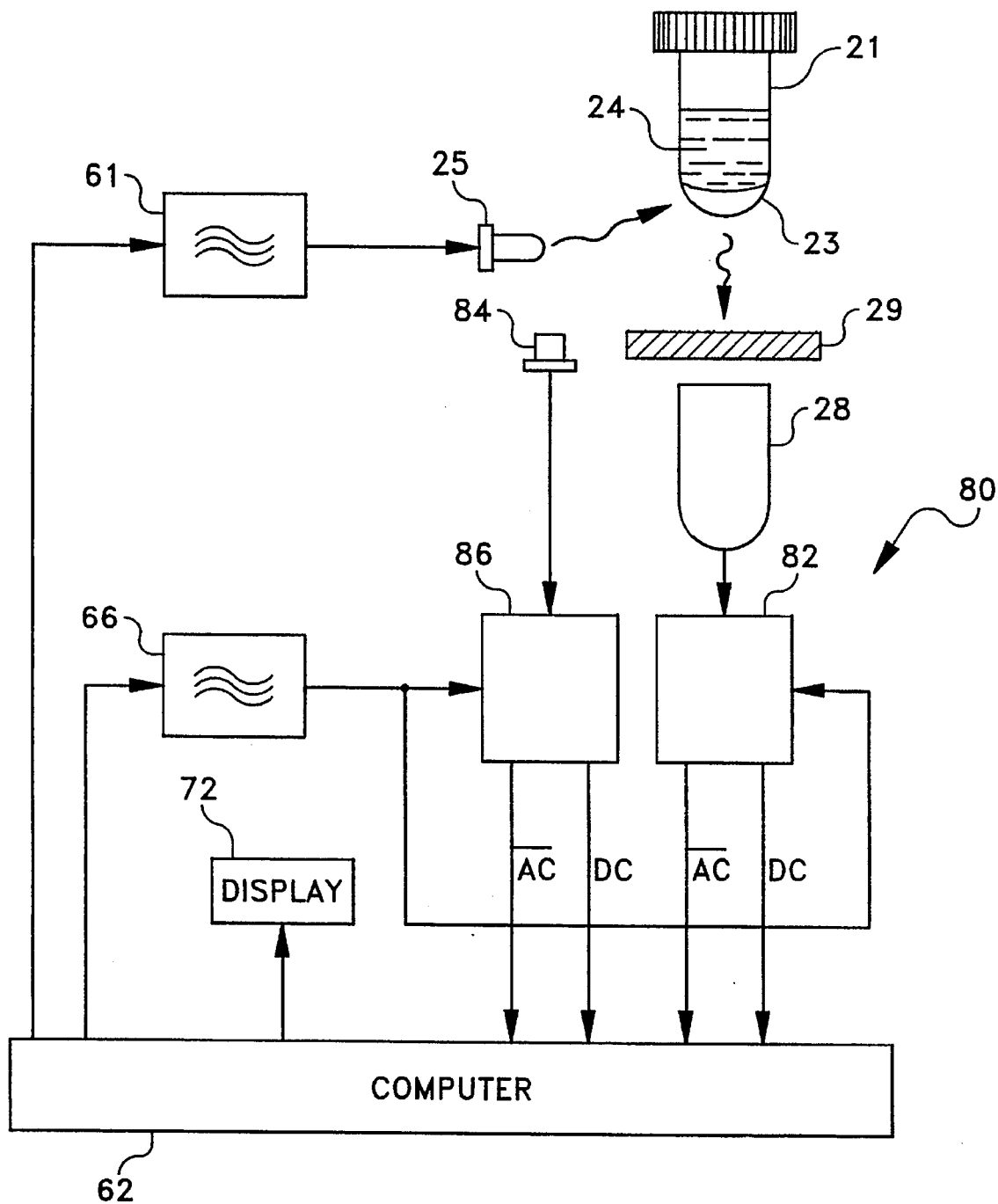
FIG. 12 is a fourth system for accomplishing the method of the present invention.

FIG. 12 shows a further embodiment 80 which also incorporates the second electronic signal source 60. FIG. 12 includes the ability to fine tune the ratio by correcting for any changes in the excitation modulation. As discussed above, one assumption made in the above calculations was that the excitation modulation would be effectively 100%. This embodiment measures and corrects for any deviation by the excitation modulation from that idealized amount. Thus, in embodiment 80, circuitry 82 for calculating the emission modulation is included which is similar to that shown in FIG. 11, Further, circuitry 86, which is also similar to that shown in FIG. 11, is used to calculate the excitation modulation. The excitation modulation is measured by a source monitor photodetector 54.

With this embodiment, one calculates both the excitation modulation and the emission modulation and then calculates a ratio which is the relative modulation m. This relative modulation is compared to the expected relative modulation as described above, and the frequency of the excitation radiation is adjusted until the measured and desired ratios are equal.

In a further feature of all of the above described systems and methods, the radiation sources are periodically turned off and DC measurements are made. This will provide an indication of the so called "dark current" signal in the environment of the vial. Such dark current signals may be the result of ambient light, etc. The ratios calculated by the inventive methods are preferably adjusted by subtracting out this dark current DC value from the measured DC value prior to calculating the ratios. In this way, the measured results more accurately monitor the actual conditions within the vial, and more accurate test results are provided.

Preferred embodiments of the instant invention have been disclosed. A worker of ordinary skill in the art would recognize, however, that certain modifications would come within the scope of this invention. For that reason the following claims should be studied in order to determine the true scope and content of this invention.

I claim:

1. A method of determining whether a sample vial containing a sample with bacteria is experiencing bacterial growth, said method comprising the steps of:
   (a) directing an excitation radiation into a fluorescent chemical sensor in a sample vial containing a sample with bacteria, said radiation having an intensity modulated at a first frequency;
   (b) measuring an AC and DC component of an intensity of a fluorescent emission from the fluorescent chemical sensor caused by the excitation radiation of step (a);
   (c) calculating a ratio based on the AC and DC components of the intensity of the fluorescent emission;
   (d) comparing the ratio calculated in step (c) to a desired ratio;
   (e) adjusting the first frequency of the excitation radiation directed into the fluorescent chemical sensor in step (a), if the ratio calculated in step (c) and the desired ratio differ;
   (f) repeating steps (a)–(e) until the ratio calculated in step (c) is equal to the desired ratio;
   (g) measuring a final adjusted frequency when step (f) is completed;
   (h) comparing the final adjusted frequency to the first frequency to determine whether the final frequency is lower than the first frequency; and
   (i) determining that the sample in the sample vial is experiencing bacterial growth, if the comparing step determines that the final adjusted frequency is lower than the first frequency.

2. A method as recited in claim 1, wherein the excitation radiation being directed into the chemical sensor in step (a) is periodically turned off, and the AC and DC components measured at that time in step (b) represent a dark signal current, and the DC component of step (b) is adjusted by the dark signal current.

3. A method as recited in claim 2, wherein there are two inputs controlling a source of radiation in step (a), with a first input controlling changes in intensity and a second input controlling changes in frequency.

4. A method as recited in claim 1, wherein the desired ratio in step (d) is equal to $1/\sqrt{3}$.

5. A method as recited in claim 1, wherein the first frequency of the excitation radiation of step (a) is used to control a second signal source generating a signal which is sent to a mixer and a second frequency of the second signal source signal being controlled to remain a small difference from the first frequency of the excitation radiation.

6. A method of determining whether a sample vial containing a sample with bacteria is experiencing bacterial growth, said method comprising the steps of:
   (a) directing an excitation radiation into a fluorescent chemical sensor in a sample vial containing a sample with bacteria, said radiation having an intensity modulated at a first frequency;
   (b) measuring an AC and DC component of an intensity of a fluorescent emission from the fluorescent chemical sensor caused by the excitation radiation of step (a);
   (c) calculating a ratio based on the AC and DC components of the intensity of the fluorescent emission;
   (d) comparing the ratio calculated in step (c) to a desired ratio selected to be indicative of the fluorescent chemical sensor operating in a high resolution area;
   (e) adjusting the first frequency of the excitation radiation directed into the fluorescent chemical sensor in step (a) to set the ratio calculated in step (c) equal to the desired ratio in step (d);
   (f) repeating steps (a)–(e) until the ratio calculated in step (c) is equal to the desired ratio;
   (g) measuring a final adjusted frequency when step (f) is completed;
   (h) comparing the final adjusted frequency to the first frequency to determine whether the final frequency is lower than the first frequency; and
   (i) determining that the sample in the sample vial is experiencing bacterial growth, if the comparing step determines that the final adjusted frequency is lower than the first frequency.

7. A method as recited in claim 6, wherein the desired ratio in step (d) is equal to $1/\sqrt{3}$.

8. A method as recited in claim 6, further comprising the step of measuring an AC and DC component of the excitation radiation directed into the sensor in step (a).

9. A method as recited in claim 8, wherein the ratio calculated in step (c) is the ratio of the AC and DC components of said emission radiation from step (b) divided by the ratio of the AC and DC components of said excitation radiation directed into the sensor in step (a).

10. A method as recited in claim 9, wherein the desired ratio in step (d) is equal to $1/\sqrt{3}$.

11. A method as recited in claim 6, wherein the excitation radiation being directed into the chemical sensor in step (a) is periodically turned off, and the AC and DC components measured at that time in step (b) represent a dark signal current, and the DC component of step (b) is adjusted by the dark signal current.

\* \* \* \* \*